(12) United States Patent
Bahrmann et al.

(10) Patent No.: US 6,472,565 B1
(45) Date of Patent: Oct. 29, 2002

(54) METHOD FOR PRODUCING ALDEHYDES

(75) Inventors: Helmut Bahrmann, Hamminkeln (DE); Hans Bohen, Moers (DE)

(73) Assignee: Celanese Chemicals Europe GmbH (DE)

( * ) Notice: Subject to any disclaimer, the term of this patent is extended or adjusted under 35 U.S.C. 154(b) by 0 days.

(21) Appl. No.: 10/048,703

(22) PCT Filed: Apr. 18, 2000

(86) PCT No.: PCT/EP00/03500

§ 371 (c)(1),
(2), (4) Date: Oct. 23, 2001

(87) PCT Pub. No.: WO00/66526

PCT Pub. Date: Nov. 9, 2000

(30) Foreign Application Priority Data

Apr. 29, 1999 (DE) .......................... 199 19 495

(51) Int. Cl.$^7$ .......................... C07C 45/49; C07C 45/50
(52) U.S. Cl. .......................... 568/454; 568/451
(58) Field of Search .................. 568/429, 444, 568/451, 454, 489

(56) References Cited

U.S. PATENT DOCUMENTS 5,113,022 A * 5/1992 Abatjoglou et al.
5,118,867 A * 6/1992 Bahrmann et al.
5,874,638 A * 2/1999 Chauvin et al.

FOREIGN PATENT DOCUMENTS

| EP | 0435084 | 7/1991 |
| EP | 0776880 | 6/1997 |
| EP | 0924182 | 6/1999 |

* cited by examiner

Primary Examiner—Sreeni Padmanabhan
Assistant Examiner—Sikarl A. Witherspoon
(74) Attorney, Agent, or Firm—Bierman, Muserlian and Lucas

(57) ABSTRACT

The invention relates to a method for producing aldehydes by reacting monoolefins, conjugated and non-conjugated polyolefins, cycloolefins, or derivatives of these classes of compounds with carbon monoxide and hydrogen (hydroformylation) in the presence of rhodium or rhodium compounds and a non-aqueous liquid of the formula $(Q^{3o})_a A^{a-}$, wherein $Q^+$ represents a singly charge ammonium cation that is optionally substituted with organic radicals, and $A^{a-}$ represents the anion of a sulphonated or carboxylated triester of phosphoric acid.

15 Claims, No Drawings

METHOD FOR PRODUCING ALDEHYDES

This application is a 371 of PCT/EP00/0500 filed Apr. 18, 2000, now WO 00/66526, published Nov. 9, 2000.

The present invention relates to a process for preparing aldehydes by reaction of olefins or olefinically unsaturated compounds with hydrogen and carbon monoxide (hydroformylation) in the presence of rhodium or rhodium compounds and a nonaqueous ionic liquid of the formula $(Q^+)_a A^{a-}$. In this formula, $Q^-$ is a singly charged ammonium cation which may be substituted by organic radicals or the equivalent of a multiply charged ammonium cation which may be substituted by organic radicals and $A^{a-}$ is the anion of a sulfonated or carboxylated triester of phosphorous acid. a is an integer equal to or greater than 1 and indicates the charge on the anion or the number of cations bearing a charge of +1 in the compounds corresponding to the formula.

Aldehydes are of great economic importance as valuable intermediates in industrial chemistry. They can be used to prepare, for example, alcohols, carboxylic acids and amines which are in turn used as starting materials for producing important end products.

Hydroformylation is among the most widely practiced industrial processes. The reaction is catalyzed by hydridometal carbonyls, preferably of metals of group VIII of the Periodic Table of the Elements. While cobalt was initially used exclusively as catalyst metal in industry, processes using rhodium as catalyst metal are gaining increasing importance.

The preparation of aldehydes by hydroformylation of olefins can be carried out by a single-phase reaction in an organic phase. Here, the catalyst, for example a rhodium/triphenylphosphine complex, is present as a solution in the reaction mixture formed by starting materials and reaction product. An organic solvent, e.g. toluene, xylene or tetrahydrofuran, may additionally be present.

Problems which arise in this process are the separation of the reaction products from the reaction mixture and the recovery of the catalysts which are homogeneously dissolved in the reaction product. This is generally achieved by distilling the reaction product from the reaction mixture. In practice, this route can only be followed in the hydroformylation of lower olefins, e.g. olefins having up to about 5 carbon atoms in the molecule, because of the thermal sensitivity of the aldehydes formed and the resulting formation of by-products with deterioration in the aldehyde yield. In addition, the thermal stressing of the material being distilled can lead to considerable losses of catalyst as a result of decomposition of the catalytically active complexes.

These drawbacks can be avoided if the hydroformylation reaction is carried out in a two-phase system. Such a process is described, for example, in DE-C 26 27 354. This process is characterized by the presence of an organic phase comprising the starting olefins and the reaction product and an aqueous phase in which the catalyst is dissolved. Catalysts used are water-soluble rhodium complexes containing water-soluble phosphines as ligands. The phosphines include, in particular, triarylphosphines, trialkylphosphines and arylated or alkylated disphosphines whose organic radicals are substituted by sulfonic acid groups or carboxyl groups. Their preparation is known from, for example, DE-C 26 27 354.

The two-phase hydroformylation process carried out in the presence of an aqueous catalyst-containing phase is particularly useful in the hydroformylation of lower olefins, particularly in the case of ethylene and propylene. On the other hand, if higher olefins such as hexene, octene or decene are used, the conversion is decreased considerably. The decrease in the conversion may well be attributable to the reduction in the solubility of higher olefins in water, since it is assumed that the reaction between the reactants occurs in the aqueous phase. This hypothesis is supported by the fact that the olefins conversion is significantly increased when a phase transfer reagent (solubilizer) is added to the aqueous catalyst solution. According to EP-B 0 562 451, solubilizers which have been found to be particularly useful are cationic solubilizers of the formula $[A-N(R^1R^2R^3)]^+E^-$, where A is a straight-chain or branched alkyl radical having from 6 to 25 carbon atoms, $R^1$, $R^2$, $R^3$ are identical or different and are straight-chain or branched alkyl radicals having from 1 to 4 carbon atoms and $E^-$ is an anion, in particular sulfate, tetrafluoroborate, acetate, methosulfate, benzenesulfonate, alkylbenzenesulfonate, toluene-sulfonate, lactate or citrate.

Carrying out the hydroformylation process in a two-phase system in the presence of an aqueous catalyst-containing phase requires not only sufficient solubility of the olefin in the aqueous phase but also sufficient stability of the olefin to be reacted toward water. Water-sensitive olefins such as acrylic esters or unsaturated acetals can thus not be used successfully in this process.

To overcome the disadvantage indicated without having to give up the advantage of the two-phase hydroformylation process, the use of nonpolar perfluorinated hydrocarbons, e.g. perfluoromethyl-cyclohexane, as nonaqueous phase immiscible with the organic reaction product has been proposed for the catalytic hydroformylation of olefins. However, specific fluorinated ligands, for example tris(1H, 1H, 2H-perfluorooctyl)phosphine are necessary to dissolve the rhodium complexes in the perfluorinated hydrocarbons (*Science* 1994, 266, 72).

Another way of carrying out catalytic reactions in a nonaqueous two-phase system is described in *CHEMTECH*, September 1995, pages 26 to 30. According to this reference, nonaqueous ionic liquids which are liquid at room temperature, e.g. a mixture of 1,3-dialkylimidazolium chloride, preferably 1-n-butyl-3-methylimidazolium chloride ($[BMI]^+[Cl]^-$ for short), and aluminum chloride and/or ethylaluminum dichloride are used as solvents for the catalyst. Examples of reactions carried out using such catalyst solutions are olefin dimerization in the presence of nickel complexes, e.g. dimerization of propene to form isomeric hexanes or dimerization of butene to form isooctenes. In these reactions, the reaction product is obtained as an upper phase, while the catalyst-containing nonaqueous ionic liquid forms the lower phase and can be isolated by simple phase separation. The solution of the catalyst in the nonaqueous ionic liquid can be reintroduced into the process.

*Am. Chem. So., Div. Pet. Chem.* 1992, 37, pages 780 to 785, discloses that a nonaqueous ionic liquid comprising $[BMI]^+[Cl]^-$ and aluminum chloride is used as a solvent in which, after addition of ethylaluminum dichloride and $NiCl_2(PR_3)_2$, where R is isopropyl, the dimerization of propene is carried out.

The use of low-melting phosphonium salts, e.g. tetrabutylphosphonium bromide, as solvent in hydroformylation reactions is described in *Journal of Molecular Catalysis*, 47 (1988) pages 99–116. According to this reference, the hydroformylation of olefins, e.g. 1-octene, is carried out using ruthenium carbonyl complexes in the presence of nitrogen- or phosphorus-containing ligands, e.g. 2,2'-bipyridyl or 1,2-bis(diphenylphosphino)ethane, at temperatures of from 120 to 180° C. to give a mixture of n-nonanol and n-nonanal. In this process, a reaction mixture having an n-nonanol content of up to 69% by weight, based on the reaction mixture, is obtained. The isolation of the desired n-nonanal therefore requires a considerable outlay for distillation.

European patent application EP-A-0 776 880 discloses the hydroformylation of olefins in the presence of quaternary ammonium and/or phosphonium salts as solvents for the catalyst. Preference is given to salts containing [BMI]$^+$ as cation.

Salts of quaternary diamines in which the cation has the formula

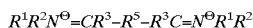
$$R^1R^2N^{\oplus}=CR^3-R^5-R^3C=N^{\oplus}R^1R^2$$

where $R^1$, $R^2$, $R^3$ are identical or different and are each hydrogen or a hydrocarbon radical having from 1 to 12 carbon atoms and $R^5$ is an alkylene radical, e.g. methylene (-CH$_2$-), ethylene (-CH$_2$-CH$_2$-) or propylene (-CH$_2$-CH$_2$-CH$_2$-), or a phenylene radical, are used as solvents for hydroformylation catalysts. Suitable anions are, for example, hexafluorophosphate, hexafluoroantimonate, tetrachloroaluminate of tetrafluoroborate. These quaternary ammonium and/or phosphonium salts are liquid below 90° C., preferably below 85° C. and particularly preferably below 50° C.

The hydroformylation catalyst dissolved in the solvents mentioned comprises cobalt, rhodium, iridium, ruthenium palladium or platinum as active metal and a tertiary phosphine or tertiary sulfonated phosphine, a tertiary arsine, tertiary stilbene or a phosphite as ligand. The molar ratio of ligand to metal is 9.5.

The catalytically active metals are used as compounds, for example rhodium in the form of dicarbonylrhodium acetylacetonate or rhodium carbonyl Rh$_6$(CO)$_{16}$. The hydroformylation catalyst is formed from them under the reaction conditions. The hydroformylation reaction is particularly preferably carried out at from 30 to 90° C.

According to *Angew. Chem.* 1995, 107, No. 23/24, pages 2941 to 2943, too, hydroformylation reactions can be carried out using 1,3-dialkylimidazolium salts which are liquid at room temperature as catalyst-containing solvent which is immiscible with the organic reaction mixture. For this purpose, dicarbonylrhodium acetyl-acetonate is added as catalyst precursor to a solution of triphenylphosphine in [BMI]$^{\ominus}$[PF$_6$]$^{\ominus}$; the molar ratio of phosphorus (III) to rhodium can vary from 3 to 10. The catalyst is preformed by means of synthesis gas (volume ratio of hydrogen to carbon monoxide=1:1). N-1-Pentene is subsequently reacted with synthesis gas of the same composition at a temperature of 80° C. In this case too, the organic product phase can be separated in a simple manner from the catalyst-containing, nonaqueous ionic liquid by decanation.

The known processes for the hydroformylation of olefins are characterized by the use of a nonaqueous ionic liquid which serves as solvent for the catalytically active metal complex. The use of the nonaqueous ionic liquid as solvent introduces additional anions which do not serve as ligands, e.g. hexafluoroantimonate or hexafluorophosphate, into the hydroformylation process.

Furthermore, the prior art (cf. *Angew. Chem.* 1995, 107, No. 23/24, pages 2941 to 2943 and EP-A-0 776 880) states that the molar ratio of phosphorus to rhodium varies in the range from 3 to 10. Higher molar ratios are obviously regarded as unsuitable, although increasing the proportion of ligand, based on the metal, should improve the stability of the catalytically active complex. It is possible that the solubility of the compounds acting as ligands in the hitherto customary ionic liquids is limited, so that they precipitate from the solution when a maximum concentration is exceeded and thus leave the catalyst phase.

Disadvantages of the known processes are not only the loss of the phosphine ligands but also the transfer of the catalytically active metal from the nonaqueous ionic liquid into the organic phase. According to the prior art, this disadvantage can be circumvented if charged ligands, e.g. monosulfonated or trisulfonated triphenylphosphine, are used in place of uncharged ligands such as triphenylphosphine, since it is to be expected that charged ligands will increase the solubility of the catalytically active metal compounds in the nonaqueous ionic liquid. Although the use of charged ligands was able to reduce the transfer of the catalytically active metal, the aldehyde yield was at the same time decreased to only 16–33% (*Angew. Chem.* 1995, 107, No. 23/24, pages 2941 to 2943, EP-A-0 776 880).

It is therefore an object of the invention to develop a process for the hydroformylation of olefins or olefinically unsaturated compounds in the presence of a catalytically active metal and a nonaqueous ionic liquid, which process avoids the disadvantages described, in particular gives the reaction products, viz. aldehydes and compounds containing aldehyde groups, in high yields, with catalyst losses not occurring or at most occurring to a minor, justifiable extent.

The invention provides a process for preparing aldehydes by reacting monoolefins, nonconjugated polyolefins, cycloolefins or derivatives of these classes of compound with carbon monoxide and hydrogen at temperatures of from 20 to 150° C. and pressures of from 0.1 to 20 MPa in the presence of a nonaqueous ionic liquid of the formula (Q$^{\ominus}$)$_a$A$^{a-}$ and at least one rhodium compound. In this process, is a singly charged ammonium cation which may be substituted by organic radicals or the equivalent of a multiply charged ammonium cation which may be substituted by organic radicals, A$^{a-}$ is the anion of a sulfonated or carboxylated triester of phosphorous acid and a is an integer equal to or greater than 1.

It has surprisingly been found that rhodium compounds dissolved in the nonaqueous ionic liquids used according to the invention are very suitable for the hydroformylation of olefins or olefinically unsaturated compounds. Ionic liquid and rhodium compound form catalyst systems (a term which will be retained in the following) which display high activity and selectivity. Their properties are probably attributable to the fact that esters of phosphorous acid have a double function. They not only act as ionic liquids as solvents for the metal compounds but can also act as ligands and form complexes (coordination compounds) with rhodium as central atom. For this reason, the term "ligand liquid" is also employed in the following for the ionic liquids. The presence of ligands, possibly in a large excess over the amount stoichiometrically required for complex formation, stabilizes the catalytically active metal compound, with the above-described result of improved catalytic behavior. Furthermore, the stabilization leads to a reduction in the noble metal losses, because significantly less rhodium is carried from the reaction mixture together with the reaction product. For this reason, the catalyst system can be recirculated to the reaction zones far more often than rhodium catalysts in the absence of a ligand liquid, without a reduction in the catalyst activity and/or selectivity being observed. Stabilized catalyst systems give higher yields of aldehydes and have a longer life than catalysts which have not been stabilized.

In this context, it is also significant that the use of nonaqueous ionic ligand liquids in the hydroformylation process allows very high P/Rh molar ratios to be employed;

the ratio P:Rh can be 1000:1 and may even be higher. The opportunity of using the phosphorus compounds in very high excess has the advantage that phosphorus losses due to transformation and degradation of the phosphorus compounds, e.g. by conversion of P(III) compounds into P(V) compounds incapable of coordination during the course of hydroformylation cycles in a continuous process or when the catalyst is repeatedly used in the case of a batch process, do not occur. This is because, firstly, the ligand liquid is present in a sufficiently large amount that the formation of coordination compounds containing phosphorus ligand is ensured by the Law of Mass Action. Secondly, the downstream products resulting from the ligands never reach a concentration, based on the ligand liquid present, which is so high that they can have an adverse effect on the reaction. From this point of view, too, rapid exhaustion of the catalyst system does not have to be feared either. Furthermore, any losses of metal and/or ligand liquid can, if necessary, be made up by introduction of fresh catalyst system or its components.

The ammonium salts of sulfonated or carboxylated phosphorous triesters used according to the invention are formally derived from phosphorous acid by esterification with the ammonium salts of hydroxysulfonic acids or hydroxycarboxylic acids of the formula

$$(Qac)_b\text{-Y-}(OH)_c \quad (1)$$

where ac is an acid radical, namely the sulfonic acid group $-SO_3^-$ or the carboxylic acid group $-COO^-$ and Q is, as already indicated above, a singly charged ammonium cation which may be substituted by organic radicals or the equivalent of a multiply charged ammonium cation which may be substituted by organic radicals.

Furthermore, Y in the formula (1) is an organic radical. Accordingly, the compounds represented by this formula are sulfonated or carboxylated hydroxy compounds derived from aliphatic, cycloaliphatic, aromatic and heterocyclic parent structures. The aliphatic compounds can be linear or branched and, like the cycloaliphatic compounds, saturated or unsaturated. The cycloaliphatic and aromatic compounds include both monocyclic and polycyclic structures. Likewise, the hydroxy acids of the phosphites used according to the invention include aliphatic-aromatic and also aromatic-aliphatic compounds. Possible heterocyclic compounds are saturated or unsaturated ring systems containing nitrogen, oxygen or sulfur as hetero atom. Two or more identical or different hetero atoms can also be present in the molecule. Furthermore, the heterocycle can also be substituted by alkyl radicals or aryl radicals or be fused with further ring systems, either aliphatic, aromatic or heterocyclic. All compounds may bear further substituents known to those skilled in the art which are chemically unreactive in their specific use as ionic liquid.

In particular, Y in the above formula (1) is a linear or branched, saturated aliphatic radical having a total of from 1 to 20 carbon atoms which may be substituted by hydroxy groups or by alkoxy radicals having from 1 to 10 carbon atoms. Y is preferably a saturated or unsaturated, monocyclic or polycyclic cycloaliphatic radical having from 5 to 14 carbon atoms in the ring or rings or a monocyclic or polycyclic aromatic radical having from 6 to 14 carbon atoms in the ring or rings. Both the cycloaliphatic radicals and the aromatic radicals may bear not only sulfonic acid or carboxylic acid radicals but also further substituents, namely alkyl radicals having from 1 to 20 carbon atoms, aryl, alkylaryl or aralkyl radicals having from 6 to 30 carbon atoms and cycloalkyl radicals having from 5 to 14 carbon atoms, also hydroxy groups and alkoxy radicals having from 1 to 10 carbon atoms. The aromatic radicals are preferably derived from benzene, from biphenyl, from naphthalene and from binaphthyl. A particularly useful arylalkyl radical has been found to be the readily available, substituted or unsubstituted benzyl radical. Alkylaryl radicals are preferably derived from toluene, ethylbenzene and the isomeric xylenes. Among the heterocycles, radicals of nitrogen-containing, saturated or unsaturated five- or six-membered rings, in particular pyridine, are of importance. Finally, b and c are each integers and are at least 1; c is particularly preferably 1 to 2.

Sulfonated or carboxylated esters of phosphorous acid according to the invention include, in particular, compounds of the formula (2)

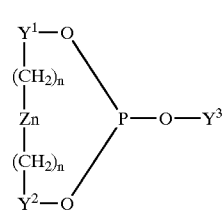

where $Y^1$, $Y^2$ and $Y^3$ are identical or different, are each an organic radical and are defined as for Y under formula (1). Z is a divalent bridging group and is $-CR^1R^2-$, where $R^1$ and $R^2$ are each, independently of one another, hydrogen or an alkyl radical having from 1 to 12 carbon atoms. Z may also be -O-, -S-, -CO-, $-CH_2-CO-CH_2-$; n are identical or different and are each 0 or 1, and when Z is $-CR^1R^2-$ are 1, 2 or 3. When n is 0, the radicals $Y^1$, $Y^1$ and $Y^3$ can be independent. However, two adjacent radicals $Y^1$ and $Y^2$, $Y^2$ and $Y^3$ or $Y^1$ and $Y^3$ can also be joined to one another and form, for example, a divalent radical. If $Y^1$ and $Y^2$ are each a radical derived from benzene, these two adjacent radicals may be, for example, linked by a single bond to form a divalent biphenyl radical. If adjacent radicals $Y^1$, $Y^2$, $Y^3$ are cycloaliphatic or aromatic structures, they can in the case of n=0 also be linearly fused. This then results, for example, in divalent, substituted or unsubstituted cycloaliphatic aromatic or cycloaliphatic-aromatic radicals, e.g. divalent dicyclodecyclene or tricyclotetradecylene radicals or divalent naphthylene or anthracylene radicals. Furthermore, the esters of the formula (2) contain at least one $ac^-$-radical, i.e. at least one sulfonic acid group or one carboxyl group.

In the compounds of the formula (2), $Y^1$, $Y^2$, $Y^3$ are each preferably a radical derived from benzene, from naphthalene, from biphenyl or from binaphthyl which may in each case be substituted by one or more alkyl radicals having from 1 to 20 carbon atoms, by one or more aryl, aralkyl, alkylaryl radicals having from 6 to 30 carbon atoms and/or by one or more cycloalkyl radicals having from 5 to 14 carbon atoms, by hydroxy groups and/or alkoxyalkyl radicals having from 1 to 10 carbon atoms and/or by one or more acid radicals (-ac⁻). Z is, in particular, the radical $-CH_2-$, -O-, -CO- or $-CH_2-O-CH_2-$.

The compounds corresponding to the formula (2) include sulfonates or carboxylates of trialkyl phosphites such as trimethyl phosphite, triethyl phosphite, butyl diethyl phosphite, tri-n-propyl phosphite, tri-n-butyl phosphite, tri-2-ethylhexyl phosphite, tri-n-octyl phosphite, tri-n-dodecyl phosphite, of dialkyl aryl phosphites such as dimethyl phenyl phosphite, diethyl phenyl phosphite, of alkyl diaryl phosphites such as methyl diphenyl phosphite, ethyl diphenyl phosphite and of triaryl phosphites such as triphenyl phosphite, phenyl biphenylene phosphite and trinaphthyl phosphite.

A further group of important sulfonated or carboxylated esters of phosphorous acid corresponding to the invention are polyphosphites of the formula (3)

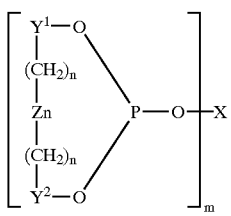
(3)

In this formula, $Y^1$ and $Y^2$ are identical or different and are as defined for Y under the formula (1) and for $Y^1$, $Y^2$ and $Y^3$ under the formula (2). The definitions of Z and n correspond to those given under the formula (2). X is an m-valent bridging group selected from among alkylene radicals, alkyleneoxyalkylene radicals, arylene radicals and aryl-$Z_n$-aryl radicals. m is an integer and is in the range from 2 to 6. Furthermore, the polyphosphite of the formula (3) contains at least one ac⁻radical, i.e. at least one sulfonate (-$SO_3^-$) or carboxylate (-$COO^-$) group.

X is preferably an alkylene radical having from 2 to 18, in particular from 2 to 12, carbon atoms or an arylene radical having from 6 to 18 carbon atoms. When X is aryl-$Z_n$-aryl, Z is preferably -$CH_2$-, -O-, -CO- or -$CH_2$-CO-$CH_2$-. The radicals X may likewise be substituted by one or more alkyl and/or alkoxy radicals and/or by one or more acid radicals (-ac⁻).

Further important representatives of the esters of phosphorous acid according to the invention have the formula (4) below.

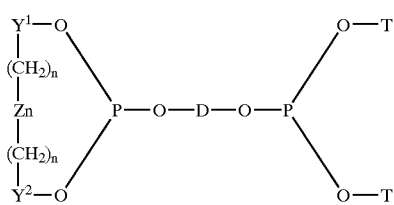
(4)

In this formula, $Y^1$ and $Y^2$ are identical or different and are as defined for Y under the formula (1) and for $Y^1$ and $Y^2$ under the formula (3). The definitions of Z and n correspond to those given under the formula (2) and the formula (3). D is a divalent hydrocarbon radical as bridging group, namely an alkylene radical having from 1 to 30 carbon atoms, an arylene, alkylarylene, arylalkylene radical having from 6 to 30 carbon atoms or an aryl-$Z_n$-aryl radical. T is a monovalent hydrocarbon radical having from 1 to 30 carbon atoms and may be an alkyl, aryl, aralkyl, alkylaryl or cycloalkyl radical. Furthermore, the phosphite of the formula (4) contains at least one ac⁻radical, i.e. at least one sulfonate (-$SO_3^-$) or carboxylate (-$COO^-$) group.

The sulfonated or carboxylated esters of phosphorous acid can be obtained by transesterification (alcoholysis) of phosphorous esters with a salt, preferably ammonium salt, of a hydroxysulfonic acid or a hydroxycarboxylic acid. For this purpose, the salt dissolved in an organic solvent is transesterified with the phosphorous ester at from 20 or 200° C., preferably from 80 to 160° C. The reactants are usually used in equivalent amounts, even though it is also possible to use an excess of either reactant. The reaction is accelerated by catalysts such as amines, sodium, sodium alkoxides, aluminum trichloride, titanic esters or dialkyl phosphites. Phosphorous esters suitable for the transesterification are derived from aliphatic or aromatic hydroxy compounds, preferably ones containing from 1 to 12 carbon atoms. Examples of phosphorous esters are trimethyl phosphite, triethyl phosphite, butyl diethyl phosphite, tri-n-propyl phosphite, tri-n-butyl phosphite, tri-2-ethylhexyl phosphite, tri-n-octyl phosphite, tri-n-dodecyl phosphite, dimethyl phenyl phosphite, diethyl phenyl phosphite, triphenyl phosphite. A preferred organic phosphite is triphenyl phosphite.

Cations $Q^+$ present in the nonaqueous ionic liquids used according to the invention are, in particular, ammonium ions substituted by organic radicals, namely ammonium ions derived from monoamines or diamines. The ammonium ions of monoamines correspond to the formulae (5) and (6)

(5)

(6)

where $R^3$, $R^4$, $R^5$ and $R^6$ are identical or different and are each hydrogen, in particular with the proviso that at least one of $R^3$, $R^4$, $R^5$, $R^6$ is not hydrogen, or a linear or branched, aliphatic hydrocarbon radical having from 1 to 20 carbon atoms, a cycloaliphatic or aromatic hydrocarbon radical having from 6 to 20 carbon atoms or an alkoxy radical having from 1 to 10 carbon atoms. Examples of such radicals are alkyl, alkenyl, cycloalkyl, aryl, alkylaryl and aralkyl radicals.

Further cations which are useful in the nonaqueous ionic liquids used according to the invention are ions which are derived from saturated or unsaturated cyclic compounds or from aromatic compounds having a trivalent N atom in a 4- to 10-membered, preferably 5- or 6-membered, heterocyclic ring. Such cations can be represented in simplified form (i.e. without indication of the precise position and number of double bonds in the molecule) by the formulae (7) and (8) below.

(7)

(8)

$R^3$ and $R^4$ in these formulae are as defined above. Examples of cyclic amines of the abovementioned type are pyrrolidine, dihydropyrrole, pyrrole, indole, carbazole, piperidine, pyridine, and the isomeric picolines and lutidines, quinoline and i-quinoline.

Preferred cations are derived from aliphatic, cycloaliphatic or aromatic diamines. They have the formulae (9) and (10)

(9)

(10)

where $R^3$, $R^4$, $R^5$, $R^6$, $R^7$ and $R^8$ are identical or different and are each hydrogen, a linear or branched aliphatic hydrocarbon radical having from 1 to 20 carbon atoms, a cycloaliphatic or aromatic hydrocarbon radical having from 6 to 30 carbon atoms, an alkylaryl radical having from 7 to 40 carbon atoms or an alkoxy radical having from 1 to 10 carbon atoms. G is an alkylene radical (-CH$^9$-)$_d$, where R$^9$ is hydrogen or a hydrocarbon radical having from 1 to 5 carbon atoms and d is an integer from 1 to 8, preferably from 2 to 6, an arylene radical having from 6 to 30 carbon atoms or an alkylenearyl radical having from 7 to 40 carbon atoms. Examples of hydrocarbon radicals, R$^3$, R$^4$, R$^5$, R$^6$, R$^7$ and R$^8$ are alkyl, alkenyl, cycloalkyl, aryl, alkylaryl or arylalkyl radicals, e.g. methyl, ethyl, propyl, i-propyl, butyl, sec-butyl, t-butyl, amyl, methylene, ethylidene, phenyl, benzyl, R$^9$ is, for example, a methyl, ethyl, n-propyl or i-propyl radical or one of the isomeric butyl radicals. Examples of G are the radicals methylene, ethylene, propylene, butylene, 1,4-phenylene, 1,4-tolylene, 1,4-xylylene, 1,1'-biphenyl-4,4'-diyl, 1,4-naphtylene, 1,1'-binaphtyl-2,2'-diyl.

Cations which are particularly useful for the nonaqueous ionic liquids used according to the invention are derived from 1-amino-3-dialkylamino-propanes of the formula (11)

$$R^{10}R^{11}N\text{-}CH_2\text{-}CH_2\text{-}CH_2\text{-}NH_2 \quad (11)$$

as diamines, where R$^{11}$ and R$^{11}$ are identical or different linear or branched alkyl radicals having from 4 to 20 carbon atoms, for example n-butyl, n-pentyl, n-hexyl, n-heptyl, i-heptyl, n-octyl, i-octyl, n-nonyl, i-nonyl, n-decyl, i-decyl, n-undecyl, i-undecyl, n-dodecyl or i-dodecyl.

Further advantageous cations for the nonaqueous ionic liquids used according to the invention are derived from the following amines: 1-amines-3-(di-n-heptyl)-aminopropane, 1-amino3-(di-i-heptyl)aminopropane, 1-amino-3-(di-n-octyl)aminopropane, 1-amino-3-(di-i-octyl)aminopropane, 1-amino-3-(di-n-nonyl)aminopropane, 1-amino-3-(di-i-nonyl)aminopropane, 1-amino-3-(di-n-undecyl)aminopropane, 1-amino-3-(di-i-undecyl)amino-propane, 1-amino-3-(di-n-dodecyl)aminopropane or 1-amino-3-(di-i-dodecyl)aminopropane.

The above-described 1-amino-3-dialkylaminopropanes are readily obtainable from N,N-(dialkyl)amines and acrylonitrile (cf. *Ullmanns Encyclopedia of Industrial Chemistry*, Vol. A2, 1985).

Finally, the diamines which give cations suitable for the nonaqueous ionic liquids used according to the invention also include heterocyclic compounds. These include saturated or unsaturated and also aromatic compounds having two trivalent N atoms in a 4- to 10-membered, preferably 5- or 6-membered, heterocyclic ring. These compounds may be substituted both on the carbon atoms and on the nitrogen atoms, preferably by alkyl radicals having from 1 to 10 carbon atoms and by phenyl radicals. They can also be fused with substituted or unsubstituted benzene rings and/or cyclohexane rings to form polycyclic structures. Examples of such compounds are pyrazole, 3,5-dimethyl-pyrazole, imidazole, benzimidazole, dihydropyrazole, pyrazolidine, pyridazine, pyrimidine, pyrazine, 2,3-, 2,5- and 2,6-dimethylpyrazine, cimoline, phthalazine, quinazoline, phenazine and piperazine. Cations of the formula (12)

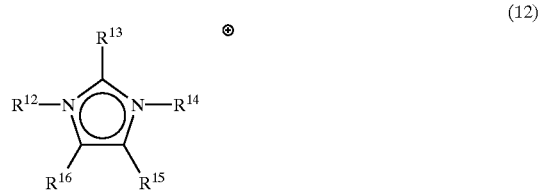

(12)

derived from imidazole and its alkyl and phenyl derivatives have been found to be particularly useful as constituents of the novel ionic liquids. In this formula, R$^{12}$, R$^{13}$, R$^{14}$, R$^{15}$ and R$^{16}$ are identical or different. They are each hydrogen, a C$_1$-C$_{30}$-alkyl radical, a C$_6$-C$_{40}$-aryl radical, a C$_7$-C$_{40}$-alkylaryl radical or an SiR$_3^{17}$ radical in which R$^{17}$ is a C$_1$-C$_{30}$-alkyl radical or a C$_6$-C$_{40}$-aryl radical. Examples of such cations are: 1-ethyl-3-methyl-2,4,5-H-imidazolium, 1-propyl-3-methyl-2,4,5-H-imidazolium, 1-butyl-3-methyl-2,4,5-H-imidazolium, 1,3,4,5-tetramethyl-2-H-imidazolium, 2,4,5-trimethyl-1,3-H-imidazolium, 1,2,3,4,5-pentamethylimidazolium, 1,2,3,5-tetramethyl-4-H-imidazolium, 1,2,3,4-tetramethyl-5-H-imidazolium, 1,3,4,5-tetraphenyl-2-H-imidazolium, 1,3-dimethyl-4,5-diphenyl-2-H-imidazolium, 1-ethyl-3-isopropyl-2,4,5-H-imidaz-olium, 1-butyl-3-octanyl-2,4,5-H-imidazolium, 1-propyl-3-octanyl-2,4,5-H-imidazolium, 1-ethyl-3-octanyl-2,4,5-H-imidazolium, 1-methyl-3-octanyl-2,4,5-H-imidazolium, 1,3-diisopropyl-4,5-dimethyl-2-H-imidazolium, 1,4,5-trimethyl-3-trimethylsilyl-2-H-imidazolium, 2-ethyl-4-methyl-1,3,5-H-imidazolium, 1,3-adamantyl-4,5-dimethyl-1-H-imidazolium, 1,2,4,5-tetramethyl-3-H-imidazolium, 1-methyl-2,3,4,5-H-imidazolium, 1,3-dimethyl-2,4,5-H-imidazolium, 2-methyl-4,5-ethyl-1,3-H-imidazolium, 2,4,5-trimethyl-1,3-H-imidazolium, 1-ethyl-2,3,4,5-H-imidazolium, 1,3-diethyl-4,5-dimethyl-2-H-imidazolium, 1,3-diphenyl-4,5-dimethyl-2-H-imidazolium, 1,3-diphenyl-2,4,5-H-imidazolium, 1,3-dimethoxy-4,5-dimethyl-2-H-imidazolium, 1-trimethylsilyl-2,3,5-trimethyl-4-H-imidazolium.

Furthermore, ionic liquids which are based on sulfonated or carboxylated triesters of phosphorous acid and whose cations are derived from polyamines have been found to be very useful. Examples of such polyamines are hexamethylenetetramine and purine and also their derivatives.

The preparation of the nonaqueous liquids used according to the invention starts out from salts of the above-described sulfonated or carboxylated esters of phosphorous acid. Suitable salts are alkali metal and alkaline earth metal salts, preferably sodium or potassium salts. They are used as aqueous solutions of the pure compounds or else as mixtures of various salts.

To obtain the nonaqueous ionic liquids used according to the invention, the amine is protonated or alkylated by means of acids and/or alkylating agents in the presence of an aqueous solution of salts of the sulfonated or carboxylated phosphorous esters to form the singly or multiply charged cation.

As acids, it is possible to use hydrogen acids, e.g. tetrafluoroboric acid or hexafluorophosphoric acid, or oxygen acids, e.g. phosphoric acid, sulfuric acid, nitric acid, also phosphonic acids having from 1 to 20 carbon atoms or sulfonic acids having from 1 to 20 carbon atoms. Preference is given to using aqueous sulfuric acid or phosphoric acid solutions which generally contain from 10 to 30% by weight of acid.

Alkylating agents which can be used are, for example, monoalkyl sulfates or dialkyl sulfates or dialkyl carbonates having from 1 to 41 carbon atoms or alkyl halides having from 1 to 10 carbon atoms.

Acid and/or alkylating agent are/is usually added in an amount of from 0.9 to 2.0, preferably from 1.0 to 1.5, equivalents per equivalent of the amines used. When using an acid, the pH after addition of the acid is from 2 to 5, preferably from 3 to 4.

To replace the metal ions in the salts of the phosphorous esters by ammonium ions, the amines are advantageously used in an excess above the stoichiometrically required amount, based on the metal ions. This excess is generally up to 5 equivalents, preferably up to 1 equivalents.

The amine is usually used as a 20–70% strength by weight, preferably 40–60% strength by weight, solution in an organic solvent. Suitable organic solvents are aliphatic or aromatic hydrocarbons such as benzene, toluene, o-xylene, m-xylene, p-xylene, mesitylene, n-heptane, n-octane, cyclohexane or else ethers such as 1,4-dioxane or tetrahydrofuran. Preference is given to using toluene or cyclohexane.

The addition of the acid and/or the alkylating agent to the mixture of the aqueous solution of the salt of salts of the phosphorous ester and the organic solution of the amine is carried out at from 0 to 60° C., preferably from 20 to 30° C. The duration of the addition is generally from 0.5 to 3 hours, preferably from 1 to 2 hours.

The reaction results in three phases: a lower aqueous phase in which the alkali metal and/or alkaline earth metal salts liberated from the esters of phosphorous acid are dissolved, a middle phase, namely the non-aqueous ionic liquid, and an upper phase comprising the organic solvent in which excess amine may be present. The desired nonaqueous ionic liquid can be obtained by simple phase separation.

To ensure satisfactory formation of the three phases, it may be advantageous to add further organic solvent to the mixture after addition of the acid and/or the alkylating agent. Preference is given to using the same organic solvent as that used for dissolving the amine. The amount of organic solvent which has to be added to achieve separation into three phases can be determined by simple preliminary tests.

In a further embodiment of the preparative method, an aqueous solution of salts of the phosphorous esters is firstly treated with an acid and/or an alkylating agent, after which the amine dissolved in an organic solvent is added. It is also possible to react the amine to be protonated and/or to be alkylated with the acid and/or the alkylating agent first and subsequently to add an aqueous solution of the salts of the sulfonated or carboxylated esters of phosphorous acid.

Finally, it is also possible to convert the salts of the sulfonated or carboxylated phosphorous esters into the free sulfonic acid or carboxylic acid by treatment with a cation exchanger in the H$^+$form and then to neutralize this acid with the amine.

The second component of the catalyst system, namely the rhodium, can be used either as metal in finely divided form, preferably on a support such as activated carbon, calcium carbonate, alumina or similar substrates, or as a rhodium compound. Examples of inorganic or organic rhodium compounds, in which rhodium can be present in its various oxidation states, are the rhodium oxides $Rh_2O$, $Rh_2O_3$, $RhO_2$, $RhO_3$, the salts of inorganic hydrogen acids such as halides, sulfides, selenides and tellurides, the salts of inorganic oxygen acids, e.g. rhodium nitrate, rhodium sulfate, rhodium perchlorate, and the salts of aliphatic monocarboxylic or poly-carboxylic acids, e.g. rhodium acetate, rhodium propionate, rhodium oxalate, rhodium malonate and rhodium 2-ethylhexanoate. Carbonyl compounds of rhodium, e.g. tricarbonylrhodium, $Rh(CO)_3$, tetracarbonylrhodium, $[Rh(CO)_4]_2$, dodecacarbonyltetrarhodium, $Rh_4(CO)_{12}$, have also been found to be very useful. Carbonyl/halide compounds such as dicarbonylrhodium bromide, $[Rh(CO)_2]Br$, and dicarbonylrhodium iodide, $[Rh(CO)_2]I$, can be used, but their use is restricted by the corrosive nature of the halide ions. Finally, rhodium complexes, in particular rhodium(III) compounds, are also suitable starting materials for preparing the catalytically active metal components in the catalyst system. These compounds contain monodentate, bidentate or tridentate ligands such as β-diketones, e.g. acetylacetone, also alkylamines, alkyl-diamines or aryldiamines, nitrogen-containing heterocycles such as pyridine or aliphatic or cyclo-aliphatic, diethylenically unsaturated hydrocarbons such as cyclopentadiene and 1,5-cyclooctadiene. Rhodium compounds which are particularly useful for forming the catalyst system are the rhodium oxides, the rhodium carbonyls, rhodium acetate, rhodium 2-ethylhexanoate and rhodium(III) acetylacetonate.

The catalyst system can be prepared in situ in the initial stage of the reaction, i.e. from ligand liquid and metallic rhodium or a rhodium compound in the reaction phase, under reaction conditions and in the presence of the olefin. However, it is also possible to preform the catalyst system separately from the hydroformylation stage in a dedicated reaction step and then to add it to the reaction mixture. T preform the catalyst system, metallic rhodium or a rhodium compound is suspended or dissolved in the ligand liquid and the mixture is treated with synthesis gas. Typical reaction conditions are temperatures of from 90 to 150° C., in particular from 100 to 120° C., and pressures of from 0.2 to 10 MPa, preferably from 0.5 to 5 MPa. The reaction time depends on the reaction conditions selected and may be up to 5 hours. The presence of an additional solvent during the preformation step is possible. Suitable solvents are aliphatic or aromatic hydrocarbons such as heptane, cycloheptane, toluene, o-xylene, m-xylene and p-xylene. The ratio of rhodium to ligand liquid (also referred to as P(III):Rh molar ratio) can vary over a very wide range and be 1000:1 and more. Useful lower limits have been found to be from 3 to 300 mol, in particular from 20 to 200 mol, of P(III) per mole of Rh.

The concentration of rhodium, based on olefin used, is from 2 to 1000 ppm by weight, preferably from 3 to 400 ppm by weight and in particular from 5 to 100 ppm by weight.

The reaction of the olefins or the olefinically unsaturated compounds with hydrogen and carbon monoxide to form carbonyl compounds is carried out at temperatures of from 20 to 150° C., preferably from 80 to 140° C. and in particular from 100 to 125° C., and pressures of from 0.1 to 20 MPa, preferably from 1 to 12 MPa and in particular from 3 to 7 MPa. The reaction conditions to be employed in an individual case also depend on the type of olefinic compounds to be reacted. Thus, reactive starting materials can be reacted at relatively low temperatures and pressures and in the presence of small amounts of catalyst, while less reactive compounds require correspondingly more energetic reaction conditions.

The composition of the synthesis gas, i.e. the proportions of carbon monoxide and hydrogen in the gas mixture, can be varied within wide limits. Use is generally made of mixtures in which the volume ratio of carbon monoxide to hydrogen is from 5:1 to 1:5. This ratio is usually 1:1 or close to this value.

The olefinic compound can be introduced into the hydroformylation either as such or as a solution. Suitable solvents are ketones such as acetone, methyl ethyl ketone, acetophenone, lower aliphatic nitriles such as acetonitrile, propionitrile or benzonitrile, dimethylformamide, linear or branched saturated aliphatic monohydroxy compounds such as methanol, ethanol, propanol and isopropanol, aromatic hydrocarbons such as benzene or toluene and saturated cycloaliphatic hydrocarbons such as cyclopentane or cyclohexane.

The process of the invention can be carried out either batchwise or continuously. After the reaction is complete, two phases, namely the less dense reaction product as upper phase and the denser catalyst solution as lower phase, are obtained. The two mixtures can be separated from one another in a simple manner, e.g. by decantation. The catalyst system can be returned partly or wholly to the hydroformylation process, and the produce can be passed to further processing, e.g. a purification process or a subsequent reaction.

The novel process is not restricted to particular olefins as starting materials. Accordingly, aliphatic, cycloaliphatic or araliphatic compounds which have one or more olefinic double bond(s) and may also contain functional groups can be reacted. Examples of aliphatic compounds are linear or branched olefins having terminal or internal double bonds, e.g. ethylene, propylene, 1-butene, isobutene, 1-pentene, 2-methyl-1-butene, 1-hexane, 1-heptene, 1-octene, 3-octene, 2,4,4-trimethyl-1-pentene, 1-nonene, 2-propyl-1-hexene, 1-decene, 3-decene, 3-undecene, 4,4-methyl-1-nonene, 6-propyl-1-decene. Conjugated polyolefins such as 1,3-butadiene can also be reacted successfully. Possible cycloaliphatic starting materials, are, for example, dicyclopentadiene, vinylcyclohexene, cyclooctadiene and cyclic terpenes such as limonene and pinene. Examples of araliphatic olefins are styrene, $\alpha$-methylstyrene, 1,1-diphenylethylene, divinylbenzene and m-hexyl-stryene.

Examples of olefinic compounds containing functional groups are alcohols, aldehydes, carboxylic acids, esters, nitriles and halogen compounds. They include vinyl compounds, in particular ethers and esters such as vinyl methyl ether, vinyl ethyl ether, $\beta$-vinylnaphthalene, o-vinyl-p-xylene, vinyl acetate; allyl compounds, in particular allyl alcohols and esters, e.g. allyl alcohol, allyl ethyl ether and allyl acetate; aldehydes such as acrolein, methacrolein, crotonaldehyde; esters of acrylic acid, of methacrylic acid, of fumaric acid and of maleic acid, acrylonitrile. This listing of suitable starting materials is not exhaustive, but merely by way of example.

The process of the invention is particularly useful for the hydroformylation of water-sensitive olefins and olefin derivatives such as the esters of vinyl alcohol, e.g. vinyl acetate, vinyl propionate, of allyl alcohol, e.g. allyl acetate, allyl propionate, allyl butyrate, the esters of acrylic acid and the acetals of acrolein. Olefins and olefin derivatives having from 2 to 20 carbon atoms can be hydroformylated particularly successfully by the novel process.

The following examples illustrate the invention without restricting its scope. The phosphite used in Example 1 was prepared by a method analogous to that reported in the literature (EP 353770).

Example 1

In a 1 1 three-necked flask provided with a bottom outlet, a solution of 65.3 g of 1-amino-3-(di-i-nonyl- amino) propane (200 mmol) in 400 ml of toluene was slowly added to room temperature to 103.9 g of the sodium salt of 4-sulfophenyl 3,3'-di-t-butyl-5,5'-dimethoxy-1,1'-biphenyl-2,2'-diyl phosphite (200 mmol) dissolved in 396 g of distilled water. While stirring, 98 g of sulfuric acid (20% strength by weight) are added dropwise over a period of 2 hours. After switching off the stirrer, 3 phases are formed, and these were separated and analyzed for P(III). All the P(III) is present in the 280 g of the middle phase, which forms the nonaqueous, ionic ligand liquid. The lower phase comprises sodium hydrogen sulfate or sodium sulfate, while the upper phase comprises mainly toluene.

Example 2

Propylene and a $CO/H_2$ mixture consisting of equal volume fractions are fed into a 0.2 l stainless steel autoclave provided with a stirrer at such a rate that 10 standard 1/h of offgas (1 standard liter is equal to 1 liter at a pressure of 1 atm and a temperature of 20° C.) can be taken from the reactor. At the same time, 280 g/h of nonaqueous, ionic ligand liquid are circulated through the reactor. Rhodium was added in the form of $RhCl_3$. The hydroformylations were carried out semicontinuously for 8 hours, with a duplicate experiment being carried out in each case to check the reproducibility. The remaining reaction parameters are given in the table.

| | | |
|---|---|---|
| Duration of the experiment [h] | 8 | 8 |
| Temperature [° C.] | 122 | 122 |
| Pressure [bar] | 50 | 50 |
| Rh content [mg/kg] | 278 | 281 |
| P(III) content [mmol/kg] | 280 | 280 |
| Ligand/Rh | 100 | 99 |
| C3 input [g/h] | 40 | 40 |
| Activity | 15.6 | 16.01 |
| Productivity | 0.222 | 0.225 |
| Conversion [%] | 39 | 41 |
| n/i ratio | 97/3 | 97/3 |

What is claimed is:
1. A Heterogeneous Hydroformylation process for the preparation of aldehydes comprising reacting an olefin selected from the group consisting of mono-olefins, conjugated and non-conjugated polyolefins, cyclo-olefins and derivatives of said olefins with carbon monoxide and hydrogen at temperatures of 20 to 150° C. and pressures of 0.1 to 20 MPa in the presence of a non-aqueous ionic liquid of the formula $(Q^+)_a A^{a-}$ and at least one rhodium compound, wherein $Q^+$ is a singly charged ammonium cation optionally substituted by organic groups or the equivalent of a multiply charged ammonium cation optionally substituted by organic groups, $A^{a-}$ is the anion of a sulfonated or carboxylated triester of phosphorous acid and a is an integer equal to or greater than 1 and wherein the aldehyde-containing product phase and the catalyst phase comprising rhodium and ionic liquid are separated from one another by phase separation and the catalyst phase is at least partly recycled to the hydroformylation process.

2. The process of claim 1, wherein the alcohol component of the phosphorous triester has the formula

$$(Qac)_b\text{-}Y\text{-}(OH)_c \qquad (1)$$

where Y is an organic group, Q is an ammonium cation optionally substituted by organic groups or the equivalent of a multiply charged ammonium cation optionally substituted by organic groups, ac is a sulfonic acid or carboxylic acid and b and c are integers which are each equal to or greater than 1, and c is 1 or 2.

3. The process of claim 2, wherein Y is saturated aliphatic of 1 to 20 carbon atoms optionally substituted by a member selected from the group consisting of hydroxy, alkoxy of 1 to 10 carbon atoms, a saturated or unsaturated, monocyclic or polycyclic cycloaliphatic of 5 to 14 carbon atoms in the ring or rings, a monocyclic or polycyclic aromatic of 5 to 14 carbon atoms in the ring or rings, a monocyclic or polycyclic aromatic of 6 to 14 carbon atoms in the ring or rings, the cycloaliphatic and the aromatic optionally substituted by a member selected from the group consisting of alkyl of 1 to 20 carbon atoms, aryl, alkylaryl and aralkyl of up to 30 carbon atoms, cycloalkyl of 5 to 14 carbon atoms, hydroxy and alkoxy of 1 to 10 carbon atoms or is a saturated or unsaturated heterocyclic containing at least one hetero atom selected from the group consisting of N, O and S in the molecule, optionally substituted by alkyl or aryl or be fused with cycloaliphatic or aromatic ring systems.

4. The process of claim 3, wherein Y is a member selected from the group consisting of benzene, toluene, ethylbenzene, isomeric xylenes, biphenyl, naphthalene, binaphthyl, benzyl and pyridine.

5. The process of claim 1, wherein the phosphorous triesters have the formula

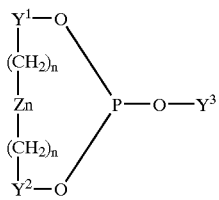

(2)

wherein $Y^1$, $Y^2$ and $Y^3$ are individually an organic member selected from the group consisting of benzene, naphthalene, biphenyl and binaphthyl, optionally substituted by at least on member of the group consisting of alkyl of 1 to 20 carbon atoms, aryl, aralkyl and alkylaryl of up to 30 carbons atoms, cycloalkyl of 5 to 14 carbon atoms, alkoxy of 1 to 10 carbon atoms and acid (–ac), Z is -CR$^1$R$^2$-, R$^1$ and R$^2$ are individually selected from the group consisting of hydrogen, alkyl of 1 to 12 carbon atoms, -O-, -S-, -CO- and -CH$_2$-CO-CH$_2$-, in particular -CH$_2$-, -O-, -CO- and -CH$_2$-CO-CH$_2$-, and n are identical or different and are each individually 0 or 1 and when Z is -CR$^1$R$^2$-, n are 1, 2 or 3, and the ester of the formula (2) contains at least one acid (–ac).

6. The process of claim 1, wherein the phosphorous triesters have the formula

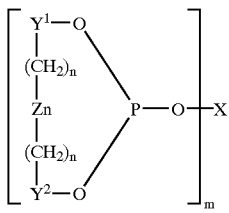

(3)

wherein $Y^1$ and $Y^2$ are individually organic selected from the group consisting of benzene, naphthalene, biphenyl and binaphthyl, optionally substituted by at least one member of the group consisting of alkyl of 1 to 20 carbon atoms, aryl, aralkyl, and alkylaryl of up to 30 carbon atoms, cycloalkyl of 5 to 14 carbon atoms, hydroxy, alkoxy of 1 to 10 carbon atoms and acid (–ac), Z is -CR$^1$-CR$^2$-, where R$^1$ and R$^2$ are selected from the group consisting of hydrogen alkyl of 1 to 12 carbon atoms, -O-, -S-, -CO-, and -CH$_2$-CO-CH$_2$-, n are individually 0 or 1, and when Z is -CR$^1$R$^2$-, n are 1, 2 or 3, X is selected from the group consisting of alkylene, alkyleneoxyalkylene, arylene and aryl-Z$_n$-aryl, and when X is aryl-Z$_n$-aryl, Z is -CH$_2$-CO-CH$_2$-, where X is optionally substituted by at least one member of the group consisting of alkyl, alkoxy and by one or more acid (–ac) and the ester of the formula (3) contains at least one acid (–ac) and m is an integer from 2 to 6.

7. The process of claim 1, wherein the phosphorous triesters hve the formula

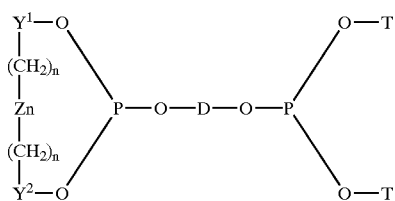

(4)

wherein $Y^1$ and$^2$ are individually selected from the group consisting of benzene, naphthalene, biphenyl and binaphthyl, optionally substituted by at least one member of the group consisting of alkyl of 1 to 20 carbon atoms, aryl, and aralkyl, and alkylaryl of up to 30 carbon atoms, cycloalkyl of 5 to 14 carbon atoms, hydroxy, alkoxy of 1 to 10 carbon atoms and acid (–ac), Z is -CR$^1$R$^2$-, R$^1$ and R$^2$ are individual selected from the group consisting of hydrogen, alkyl of 1 to 12 carbon atoms, -O-, -S-, -CO- and -CH$_2$-CO-CH$_2$-, n are individually 0 or 1 and when Z is -CR$^1$R$^2$-, n are 1, 2 or 3, D is selected from the group consisting of alkylene of 1 to 30 carbon atoms, arylene, alkylarylene and arylalkylene or up to 30 carbon atoms and aryl-Z$_n$-aryl and T is a monovalent hydrocarbon of 1 to 30 carbon atoms, and the ester of the formula (4) contains at least one acid (–ac).

8. The process of claim 1, wherein the cations in the sulfonated or carboxylated phosphorous triesters are ammonium ions derived from monoamines having the formula

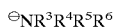

(5) or

(6)

wherein R$^3$, R$^4$, R$^5$ and R$^6$ are individually selected from the group consisting of hydrogen, with the proviso that at least one of R$^3$, R$^4$, R$^5$, R$^6$ is not hydrogen, aliphatic hydrocarbon of 1 to 20 carbon atoms, cycloaliphatic or aromatic hydrocarbon of 6 to 20 carbon atoms and alkoxy of 1 to 10 carbon atoms with the proviso that at least one of R$^3$, R$^4$, R$^5$, R$^6$ is not hydrogen.

9. The process of claim 1, wherein the cations in the sulfonated or carboxylated phosphorous triesters are ammonium ions derived from monoamines having the formula

(7)

or

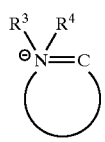

(8)

derived from saturated or unsaturated cyclic compounds or from aromatic compounds having a trivalent N atoms in a 4- to 10-membered ring, R$^3$, R$^4$ are individually selected from the group consisting of hydrogen, aliphatic hydrocarbon of 1 to 20 carbon atoms, cycloaliphatic or aromatic hydrocarbon of 6 to 20 carbon atoms and alkoxy 1 to 10 carbon atoms.

10. The process of claim 1, wherein the cations in the sulfonated or carboxylated phosphorous triesters are ammonium ions derived from diamines and having the formula $$R^3R^4R^5N^\ominus\text{-G-}N^\ominus R^6R^7R^8 \quad (9) \text{ or}$$

$$R^3R^4N^\ominus=CR^5\text{-G-}R^5C=N^\ominus R^5R^4 \quad (10)$$

wherein $R^3$, $R^4$, $R^5$, $R^6$, $R^7$ and $R^8$ are individually selected from the group consisting of hydrogen, aliphatic of 1 to 20 carbon atoms, cycloaliphatic or aromatic hydrocarbon of 6 to 30 carbon atoms, alkylaryl of 7 to 40 carbon atoms and alkoxy of 1 to 10 carbon atoms, G is $(\text{-CH}^9\text{-})_d$, $R^9$ is hydrogen or a hydrocarbon of 1 to 5 carbon atoms and d is an integer from 1 to 8, an arylene radical of 6 to 30 carbon atoms or an alkylenearyl radical of 7 of 40 carbon atoms.

11. The process of claim 1, wherein at least from 3 to 300 mol, of phosphorous (III) are used per mole of rhodium.

12. The process of claim 1, wherein the rhodium concentration, based on olefin used, is from 2 to 1000 ppm by weight.

13. The process of claim 1, wherein the reaction is carried out at temperatures of 100 to 125° C.

14. The process of claim 1, wherein the reaction is carried out at pressures of 3 to 7 MPa.

15. The process of claim 1, wherein olefins and olefin derivatives of 2 to 20 carbon atoms are reacted.

* * * * *